United States Patent
Fischer et al.

(10) Patent No.: US 7,723,370 B2
(45) Date of Patent: May 25, 2010

(54) 1, 2-DIARYL PYRAZOLES USEFUL AS ANALGETIC AND ANTIINFLAMMATORY AGENTS

(75) Inventors: János Fischer, Budapest (HU); Istvánné Kis-Varga, Kakucs (HU); György Szabo, Budapest (HU); János Leibinger, Budapest (HU)

(73) Assignee: Richter Gedeon Vegyeszeti Gyar RT., Budapest (HU)

( * ) Notice: Subject to any disclaimer, the term of this patent is extended or adjusted under 35 U.S.C. 154(b) by 290 days.

(21) Appl. No.: 11/989,439

(22) PCT Filed: Jul. 27, 2006

(86) PCT No.: PCT/HU2006/000063

§ 371 (c)(1),
(2), (4) Date: Jan. 24, 2008

(87) PCT Pub. No.: WO2007/012906

PCT Pub. Date: Feb. 1, 2007

(65) Prior Publication Data

US 2009/0036510 A1    Feb. 5, 2009

(30) Foreign Application Priority Data

Jul. 29, 2005    (HU) .................................. P0500730

(51) Int. Cl.
A61K 31/415 (2006.01)
A61P 29/00 (2006.01)
C07D 231/12 (2006.01)
(52) U.S. Cl. .................................. 514/406; 548/375.1
(58) Field of Classification Search ........................ None
See application file for complete search history.

(56) References Cited

U.S. PATENT DOCUMENTS

| 6,436,967 B1 * | 8/2002 | Talley et al. | 514/341 |
| 2005/0032851 A1 | 2/2005 | Talley et al. | 514/357 |
| 2006/0111326 A1 | 5/2006 | Rosales et al. | 514/94 |

FOREIGN PATENT DOCUMENTS

WO    WO 9515316    6/1995

OTHER PUBLICATIONS

Bombardier et al: "Comparison of upper gastrointestinal toxicity of rofecoxib and naproxen in patiens with rheumatic arthritis" N. Engl J Med 343(21): 1520-1528, Nov. 2000.
Murkherjee et al: "Risk of cardiovascur events associated with selective COX-2 inhibbitors" JAMA, 2001; 286:954-959.

* cited by examiner

Primary Examiner—Kamal A Saeed
(74) Attorney, Agent, or Firm—Jonathan Myers; Andrew Wilford

(57) ABSTRACT

The present invention relates to new compounds of formula (I), (I) wherein the meaning of $R_1$ is hydrogen atom, $C_1$-$C_5$ acyl group, benzoyl group or $R_2$—$COOR_3$ group, Y is hydrogen atom or alkali ion, $R_2$ is $C_1$-$C_4$ straight or branched alkylidene group and $R_3$ is hydrogen atom, $C_1$-$C_4$ alkyl group or alkali ion, and/or stereoisomers and/or diastereomers and/or pharmaceutically acceptable salts and/or hydrates and/or solvates thereof, which are suitable for the treatment of pain of acute and chronic inflammation origin as well as postoperative pain and dysmenorrhea. The invention also relates to the process of the synthesis of compounds of formula (I) as well as the pharmaceutical composition containing the same and the use for treatment of pain, inflammation and disorders associated with inflammation.

8 Claims, No Drawings

1, 2-DIARYL PYRAZOLES USEFUL AS ANALGETIC AND ANTIINFLAMMATORY AGENTS

CROSS REFERENCE TO RELATED APPLICATIONS

This application is the US national phase of PCT application PCT/HU2006/000063, filed 27 July 2006, published 01 Feb. 2007 as WO 2007/012906, and claiming the priority of Hungarian patent application PO500730 itself filed 29 Jul. 2005, whose entire disclosures are herewith incorporated by reference.

The invention relates to new compounds of formula (I) and/or stereoisomers and/or diastereomers and/or salts and/or hydrates and/or solvates thereof, which are useful in treating pain originated from acute and chronic inflammation as well as surgical action and dysmenorrhea. Furthermore the invention relates to the synthesis of compounds of formula (I) and the pharmaceutical compositions containing them.

DESCRIPTION OF THE PRIOR ART

It is known, that selective cyclooxygenase-2 (COX-2) enzyme inhibitors have significantly more advantageous gastrointestinal side-effect profile than the traditional non-steroid anti-inflammatory agents, however, concerning the cardiovascular side-effect profile long-term use of both the traditional non-steroid anti-inflammatory agents both the coxibs can cause cardiovascular side-effects (L. A. Garcia Rodriguez, Annals of the Rheumatic Diseases 2005, 64 (Suppl. III) page 40). Celecoxib is the most advantageous in this respect, as its cardiovascular side-effects are less pronounced.

Celecoxib is described in the European patent EP 731795. Certain problems arose during the use of it. On the one hand celecoxib is not effective in all cases of patients therefore the research for more effective analogous drugs have started. On the other hand it is desirable to reduce the gastrointestinal side-effects. It is known from the literature that the research was focused on increasing the selective inhibition of COX-2 enzyme in order to decrease the gastrointestinal side-effects. This raises the question of cardiovascular side-effects, as according to the previous observations increasing the selectivity of COX-2 inhibition resulted in increasing cardiovascular side-effects. This was proved by the so called "VIGOR-study" of the first generation COX-2 enzyme inhibitor rofecoxib (Bombardier C, Laine L, Reicin A et al for the VIGOR Study Group. *Comparison of upper gastrointestinal toxicity of rofecoxib and naproxen in patients with rheumatoid arthritis.* N Engl J Med 343(21): 1520-1528, November 2000.). The possible reasons of this phenomenon are described in the study of D. Mukherjee (Mukheijee D, Nissen S E, Topol E J. *Risk of cardiovascur events associated with selective COX-2 inhibitors.* JAMA 2001; 286:954-959).

Our aim was to synthesize analogous compounds, which are more effective than celecoxib and have less undesirable side-effects, on the other hand their COX-1/COX-2 selectivity remains unchanged.

SUMMARY OF THE INVENTION

Surprisingly it was found, that some of celecoxib derivatives are more effective analgetic and anti-inflammatory agents than celecoxib, furthermore they do not have in vitro COX-1 and COX-2 inhibitory activity and their gastrointestinal side-effect profile is essentially more favorable, as well as they have cardioprotective activity.

The present invention relates to new compounds of formula (I),

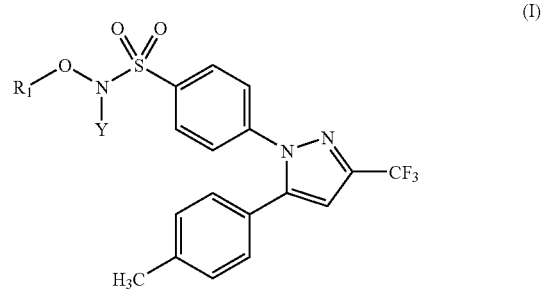

wherein the meaning of $R_1$ is hydrogen atom, $C_1$-$C_5$ acyl group, benzoyl group or $R_2$—$COOR_3$ group, Y is hydrogen atom or alkali ion, $R_2$ is $C_1$-$C_4$ straight or branched alkylidene group and $R_3$ is hydrogen atom, $C_1$-$C_4$ alkyl group or alkali ion, and/or stereoisomers and/or diastereomers and/or pharmaceutically acceptable salts and/or hydrates and/or solvates thereof. The invention also relates to the process of their synthesis as well as the pharmaceutical composition containing the same and the use for treatment of pain, inflammation and disorders associated with inflammation.

DETAILED DESCRIPTION OF THE INVENTION

The present invention relates to new compounds of formula (I),

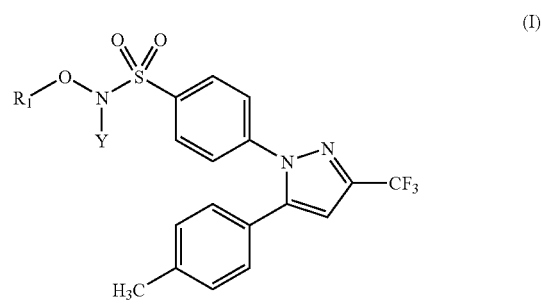

wherein the meaning of $R_1$ is hydrogen atom, $C_1$-$C_5$ acyl group, benzoyl group or $R_2$—$COOR_3$ group, Y is hydrogen atom or alkali ion, $R_2$ is $C_1$-$C_4$ straight or branched alkylidene group and $R_3$ is hydrogen atom, $C_1$-$C_4$ alkyl group or alkali ion, and/or stereoisomers and/or diastereomers and/or pharmaceutically acceptable salts and/or hydrates and/or solvates thereof.

In the meaning of Y and $R_2$ the alkali ion is preferably sodium.

The invention also relates to solvates and hydrates of compounds of formula (I).

In those cases when compounds of formula (I) have chiral centre both stereoisomers and the racemic mixture of them are subject of the invention.

The invention also relates to the process of the synthesis of compounds of formula (I) and the chemical and pharmaceutical manufacture of pharmaceutical compositions containing the same, as well as the methods of treatment and/or prevention with these compounds, which means administering to a mammal—including human—to be treated effective amount/amounts of compounds of formula (I) of the present invention as such or as medicament.

Claisen reaction of the commercially available p-methyl-acetophenone and trifluoroacetic acid ethyl ester gave 4,4,4-trifluoro-1-(4-methylphenyl)-butane-1,3-dione in good yield. The latter was further reacted with the commercially available p-hydrazino-benzenesulfonic acid in an inert solvent in the presence of hydrochloric acid to give the new 4-(5-p-methyl-phenyl)-3-trifluoromethyl-pyrazol-1-yl)-benzenesulfonic acid of formula (III) (yield over 80%),

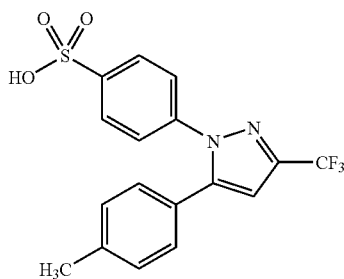

(III)

which after recrystallization from an inert solvent, preferably from diisopropyl ether, can be obtained in high purity as key substance. The new intermediate of formula (III) is transformed into 4-(5-p-methylphenyl-3-trifluoromethyl-pyrazol-1-yl)-benzenesulfonyl chloride of formula (II)

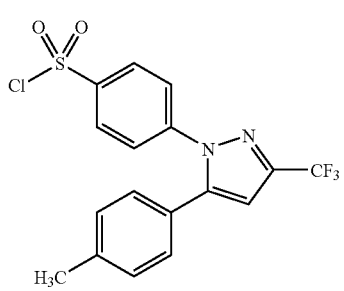

(II)

with phosphorous pentachloride in an inert solvent, preferably in dry dichloromethane.

The obtained compound of formula (II) is reacted with hydroxylamine in an inert solvent, preferably in a mixture of water and dioxane, to furnish compound of formula (I), wherein the meaning of $R_1$ is hydrogen atom. The reagent is formed in situ in the reaction mixture from hydroxylamine hydrochloride and sodium acetate. If compound of formula (II) is reacted with an aminooxy-alkane acid in an inert solvent, preferably in dioxane, those products of formula (I) are formed in high yield, wherein the meaning of $R_1$ is $R_2$—$COOR_3$ group, wherein the meaning of $R_2$ is $C_1$-$C_4$ straight or branched alkilydene group and $R_3$ is hydrogen atom or $C_1$-$C_4$ alkyl group or alkali atom. If desired the obtained compounds of formula (I) can be purified by recrystallization from an inert solvent, preferably from toluene.

Those compounds of formula (I), wherein the meaning of $R_3$ is hydrogen atom, can be transformed into alkali salts with alkali hydroxide solution, preferably with two equivalent of sodium hydroxide. The formed disodium salt can contain hydrate as solvate, preferably monohydrate.

If compound of formula (II) is reacted with O-acylated hydroxylamine in an inert solvent, preferably in dioxane, those compounds of formula (I) are formed in high yield, wherein the meaning of $R_1$ is $C_1$-$C_5$ acyl group or benzoyl group.

The invention also relates to pharmaceutical compositions containing compounds of formula (I) as an active ingredient.

Compounds of formula (I) can be used in treating of inflammation and disorders associated with inflammation, for example as an analgesic agent in treatment of pain and headache.

Compounds of formula (I) and/or stereoisomers and/or diastereomers can be used as such and/or pharmaceutically acceptable salts and/or hydrates and/or solvates thereof as medicament, usually as a standard composition. The present invention also relates to pharmaceutical compositions containing a new compound of formula (I) and/or stereoisomers and/or diastereomers and/or pharmaceutically acceptable salts and/or hydrates and/or solvates thereof as well as one or more pharmaceutically acceptable adjuvant and auxiliary material.

Compounds of formula (I) and/or geometric isomers and/or stereoisomers and/or diastereomers and/or pharmaceutically acceptable salts and/or hydrates and/or solvates thereof may be administered by any convenient method, for example by oral, parenteral buccal, sublingual, nasal, rectal or transdermal administration and the pharmaceutical compositions adapted accordingly. Pharmaceutical compositions containing compounds of formula (I) and/or geometric isomers and/or stereoisomers and/or diastereomers and/or pharmaceutically acceptable salts and/or hydrates and/or solvates thereof when given orally can be formulated as liquids or solids, for example syrups, suspensions or emulsions, tablets, capsules and chewable tablets.

Liquid formulations of compounds of formula (I) and/or geometric isomers and/or stereoisomers and/or diastereomers and/or pharmaceutically acceptable salts and/or hydrates and/or solvates thereof generally consist of a suspension or solution of a compound of formula (I) in an appropriate liquid carrier(s), for example an aqueous solvent, such as water, ethanol or glycerine or a non-aqueous solvent, such as polyethylene glycol or an oil. The pharmaceutical composition can also contain a suspending agent, preservative, flavoring and coloring agents.

A composition in the solid form of tablet can be prepared using any suitable pharmaceutical carrier(s), which are commonly used in practice, such as magnesium stearate, starch, lactose, saccharose, cellulose etc.

A composition in the solid form of capsule can be prepared using routine encapsulation procedures. For example, pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Typical parenteral compositions consist of a solution or suspension of the compound of formula (I) and/or geometric isomers and/or stereoisomers and/or diastereomers and/or pharmaceutically acceptable salts and/or hydrates and/or solvates thereof in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Biological Evaluation

In vitro Measurements

The compounds of our invention did not have COX-2 enzyme inhibition activity at 10 μM concentration—according to spectrophotometric TMPD measurements (K. Gierse, S. D. Hauser, D. P. Creely, C. M. Koboldt, S. H. Rangwala, P. C. Isakson and K. Seibert, 1995: *Expression and selective inhibition of the constitutive and inducible forms of human cyclo-oxygenase*. Biochem. J. 305: 479-48)

In vivo Assays

1. Inhibition of Carrageenan Induced Oedema in Rats

Oedema was induced by subcutaneous injection of 50 μl of 1% carrageenan (CARR) suspension in the subplantar region of the right hind paw of male Wistar rats (140-150 g). The injected carrageenan induced paw inflammation. The oedema, i.e. the difference between the pre- and post-treatment volume (in ml) of the injected hind-paw was measured using a water displacement plethysmometer (Ugo Basile, type: 7150). The treated paw was immersed up to the tibiotarsal articulation into the chamber and the volume of displaced liquid was determined as the degree of the inflammation.

Degree of inflammation (ml)=volume after the CARR treatment (ml)−volume before the CARR treatment (ml)

The degree of the anti-inflammatory effect of the treated group (which obtained test agent) was compared to that of the control group (which obtained only vehicle). The test compound and the vehicle were given orally by blunt-ended needle cannula one hour before the CARR treatment. The volume of the treated paw was measured at 3 and 5 hours after the CARR treatment and the change in the degree of inflammation in % was calculated according to the following formula:

Anti-inflammatory activity %=100×[control group (ml)−treated group (ml)/control group (ml)]

Celecoxib and the compounds of the invention were measured in 1-10-30 mg/kg p.o. dose (n=12 animal/group). Anti-inflammatory activity of the compounds was determined in % at 4 and 6 hours after p.o. treatment and $ED_{30}$ was calculated.

Results:

inhibition of the oedema by Celecoxib: was effective at 4 hours after treatment with an $ED_{30}$ of 23 mg/kg. The anti-inflammatory activity of the Celecoxib at 6 hours after the treatment was less than 30% as compared to the control group. Compound of Example 5: was potent at 4 and 6 hours after treatment with an $ED_{30}$ of 5.7 mg/kg and $ED_{30}$ of 8.4 mg/kg respectively. The obtained results show that compound of Example 5 as compared to Celecoxib significantly inhibited paw oedema at both investigated time points.

TABLE 1

| Test compound | Anti-inflammatory activity after treatment | Inhibiton of carrageenan induced edema % | | | $ED_{30}$ mg/kg |
|---|---|---|---|---|---|
| | | 3 mg/kg | 10 mg/kg | 30 mg/kg | |
| Celecoxib p.o. | 4 hours | 16 ± 3 | 24 ± 4 | 32 ± 5 | 23.0 |
| | 6 hours | 12 ± 4 | 18 ± 2 | 26 ± 4 | >30 |
| Compound of Example 5 p.o. | 4 hours | 21 ± 3 | 40 ± 4 | 49 ± 5 | 5.7 |
| | 6 hours | 20 ± 3 | 34 ± 5 | 40 ± 4 | 8.4 |

2. Carrageenan Induced Acute Hyperalgesia in Rats (Randall-Selitto Model)

Oedema (inflammation) was induced by subcutaneous injection of carrageenan (CARR) suspension in the subplantar region of the right hind paw of male Wistar rats, weighted 140-190 g (n=8-12 animal/group). The nociceptive thresholds of the inflamed hind paw after painful mechanical stimuli were measured with analgesimeter (Ugo Basile, type: 37215, Italy). The apparatus is suitable for the measuring of the extent and the latency of the pain reaction threshold of the sensitized paw after painful stimuli. The analgesics elevate the low pain reaction threshold of inflamed paw and the degree of its antinociceptive effect is expressed in reversal %.

An increasing pressure was applied to the paw and the withdrawal threshold was determined as the first sign (squeaking and/or struggling) of pain response. The pressure threshold was shown in grams. The average value of the hind paw withdrawal obtained with untreated right paw was regarded as the basal hind paw withdrawal (average 80-110 grams.) After determining the baseline threshold the animals received carrageenan injection that produced an intense inflammation associated with hyperalgesia. The mechanical threshold was determined at various times to establish the magnitude and duration of the hyperalgesia. The maximum reduction in threshold was measured 2-3 h after injection (the pain threshold of the inflamed paw is 20-30 g, which was decreased by 65-80% in comparing to the basic value).

Acute hyneralgesia model: the animals were treated with the test compounds and celecoxib (10 and 30 mg/kg p.o.) one hour after CARR treatment (100 μl 2% suspension). Pain threshold was measured at 2 and 4 hours after the treatment. Chronic hyperalgesia model: extended inflammation and decreased pain threshold were induced with higher dose of CARR. Pain threshold of inflamed paw was measured 24 hours after CARR treatment (150 μl, 2% suspension) then test compound and Celecoxib (30 mg/kg p.o.) were given to the animals. Pain threshold of treated paw was measured from 30 minutes till 3 hours after treatment.

Control groups in both models after CARR treatment were treated with vehicle p.o. at the same intervals as the test compounds. In both models the analgesic effect of the compounds was expressed in the reversal (%) of the decrease of the pain threshold.

Reversal %=[mean of treated group$_{Txh}$(g)−treated group$_{T0h}$(g)]/[basic mean of treated group$_{T-1h}$(g)−treated group$_{T0h}$(g)]

T−1 h=mean of the pain threshold of paw before CARR treatment in acute model (g)

T0h=mean of the pain threshold before treatment 1 hour after CARR treatment in acute model (g)

T×h=pain threshold after CARR treatment in the measuring times (1 h, 2 h, 3 h) in acute model (g)

In both models (acute and chronic treatment) Celecoxib in 30 mg/kg p.o. dose showed partial analgesic effect (24% and 54% reversal). In the acute model the test compound in 30 mg/kg p.o. dose showed almost complete reversal % (90%), so the test compound showed significantly better anti-inflammatory/analgesic effect as compared to the reference compound.

In the chronic model test drug showed 54% reversal, comparable with Celecoxib analgesic effect.

TABLE 2 acute model

| Acute model | Dose (mg/kg p.o.) | Analgesic effect (reversal %) after p.o. treatment | | |
|---|---|---|---|---|
| | | 1 hour | 2 hour | 3 hour |
| Celecoxib p.o. | 10 | 0 | 0 | 0 |
| | 30 | 24 | 3 | 0 |
| Compound of Example 5 | 10 | 24 | 30 | 15 |
| | 30 | 89 | 59 | 35 |

TABLE 3 chronic model

| Acute model | Dose (mg/kg p.o.) | Analgesic effect (reversal %) after p.o. treatment | | | | |
|---|---|---|---|---|---|---|
| | | 30 min | 1 hour | 2 hour | 3 hour | 4 hour |
| Celecoxib p.o. | 10 | 24 | 17 | 0 | | |
| | 30 | 54 | 34 | 34 | 26 | 20 |
| Compound of Example 5 | 10 | 23 | 22 | 28 | 14 | 11 |
| | 30 | 42 | 54 | 34 | 19 | 19 |

3. Measurement of Gastrointestinal Side Effects a) Gastric Lesions Induced by Acidified Alcohol Male Wistar rats weighing 140-160 g were treated p.o. with a 1:0.02 mixture of dry ethanol and concentrated HCl (0.5 ml) in order to induce gastric lesions. One hour later the animals were euthanized with ether and the stomach excised along its greater curvature, the mucosa was examined for the presence of lesions.

Severity of lesions:

1: petechiae or erosion with length of 1 mm
2: erosion with length between 2 and 3 mm
3: erosion with length between 3 and 4 mm
4: erosion with length between 4 and 5 mm If the lesion was longer than 5 mm, it was scored 4 point as many times as the total length of the lesion divisible by four and the rest of the length was evaluated according to the above scale. The degree of injury of mucosa was characterized by ulcer index. Ulcer index (severity of lesion×number of lesion) was calculated for every animal and the degree of injury of mucosa in the groups of tested animals was characterized by the mean of ulcer index of different groups of animals.

Test compounds were given p.o. 40 minutes before the ethanol+HCl treatment

TABLE 4

Alcohol induced mucosa injury in rats (n = 10)

| Compound | Dose mg/kg p.o. | Ulcer index |
|---|---|---|
| Methylcellulose | — | 60.8 ± 4.1 |
| Celecoxib | 30 | 49.4 ± 4.5 |
| Compound of Example 5 | 30 | 35.0 ± 4.4* |
| Methylcellulose | — | 66.2 ± 1.7 |
| Compound of Example 5 | 15 | 43.0 ± 4.4 |
| | 60 | 15.8 ± 2.8* |
| Methylcellulose | — | 97.8 ± 2.8 |
| Celecoxib | 15 | 80.6 ± 2.3 |
| | 60 | 44.4 ± 6.4* |

*p < 0.05

It can be seen from the above data that both celecoxib and the compound of the invention inhibited the alcohol induced mucosa injury, but the compound of the invention was significantly ($p<0.05$) more effective than celecoxib.

b) Acetic Acid Induced—Chronic—Gastric Ulcer

In our experiments the method d with ether and 20% acetic acid (0.05 ml) was subserosally injected in the glandular of Okabe et al was used. Male Wistar rats of 150-170 g were narcotize part of the stomach.

The test compound was given p.o. on the fifth day after the operation for seven days. The animals were euthanized with ether after 24 hours of the last dose and the abdomen was macroscopically examined (exravasation, accretion), the stomach was excised and the diameters of ulcers were measured.

TABLE 5

Acetic acid induced chronic gastric ulcer in rats

| Compound | Dose mg/kg p.o. | Change of bodyweight (g) + (increase) − (decrease) | Area of ulcer (mm²) |
|---|---|---|---|
| Methylcellulose | — | +58 ± 3 | 3.0 ± 0.8 |
| Indometacin | 2.0 | +2 ± 0.6 | 39.0 ± 5** |
| Celecoxib | 30 | +32 ± 4 | 8.2 ± 2.0* |
| Example 5 | 30 | +43 ± 5 | 2.4 ± 0.7 |

*p < 0.05;
**p < 0.01

Recovery of acetic acid induced ulcer—which is analogous to the human ulcer—was inhibited significantly by celecoxib, while compound of Example 5 did not influence it.

4. Measurement of Cardioprotective Effect

Effect of compound of Example 5 and celecoxib was determined in experimental myocardial ischemia-reperfusion induced injury.

Myocardial infarction was produced in male, SPRD CFY rats of 300-360 g by surgical occlusion of left anterior descending coronary artery. Briefly, the animals were anesthetized with pentobarbital (60 mg/kg i.p.) and the chest was opened, the left coronary artery was ligated for 6 minutes followed by reperfusion. Test compounds were administered i.p. in 30 and 60 mg/kg dose 30 minutes before occlusion of the coronary artery. The control group was treated with vehicle (5% TWEEN 80 in isotonic NaCl, 2 mg/kg).

During the myocardial ischemia-reperfasion the applied pre-treatments did not influence the heart rate and the mean blood pressure of the animals.

The frequency of arrhythmia during the 6 minutes coronary artery ligation did not alter in the different groups. In those animals which were pre-treated with compound of Example 5 (30 mg/kg) the occurrence of the serious, not mortal ventricular fibrillation, developed during reperfusion, was decreased (60% vs. 90% in the control group).

5. Measurement of Anti-hypertensive Activity in Rabbit

Anti-hypertensive activity of celecoxib and compound of Example 6 (in a dose of 30 mg/kg p.o.) was compared in New Zealand white rabbits of 2.5-3.0 kg. Molsidomine was used as reference compound in 2 mg/kg dose. Compound of Example 6 showed similar anti-hypertensive activity as molsidomine ($p<0.05$), while celecoxib did not have such effect.

Summarising the biological results it can be seen, that according to in vivo experiments pharmacological efficacy of compounds of our invention both in extent and duration exceeds that of the reference compound celecoxib.

In CARR induced oedema test anti-inflammatory activity of compounds of Examples 5 and 6 was significantly (p<0.05) higher, than that of celecoxib. In the inflammation induced chronic hyperalgesia model compound of Example 5 showed significant analgesic effect (p<0.01) and its duration of action was several hours longer than that of the reference compound.

In comparing the gastrointestinal and cardiovascular effects compounds of Examples 5 and 6 of our invention showed significantly more favourable side-effect profile than the reference compound celecoxib.

EXAMPLES

The invention is illustrated by the following not limiting examples.

Example 1

4,4,4-trifluoro-1-(4-methyl-phenyl)-butane-1,3-dione

Sodium metal (5.76 g, 0.25 mol) was dissolved in methanol (80 ml), then trifluoroacetic acid (22 ml, 0.168 mol) was added at room temperature, followed by dropwise addition of methyl-acetophenone (21.04 g, 0.165 mol). The obtained mixture was stirred at 80° C. for 10 h, the reaction mixture was concentrated in vacuo and the residue was dissolved in water (50 ml). The solution was acidified by addition of 1N hydrochloric acid (120 ml), extracted with ethyl acetate (2×80 ml), dried over MgSO$_4$, filtered and concentrated in vacuo to yield 34.60 g (95%) of the title compound. The obtained crystalline product was used in the next step without further purification.

Example 2

4-(5-p-methylphenyl-3-trifluoromethyl-pyrazol-1-yl)-benzenesulfonic acid

To a stirred suspension of p-hydrazino-benzenesulfonic acid (42 g, 0.223 mol) in ethanol (450 ml) 6N hydrochloric acid (74 ml, 0.446 mol) was added at room temperature, followed by addition of 4,4,4-trifluoro-1-(4-methyl-phenyl)-butane-1,3-dione (51.45 g, 0.223 mol). The obtained suspension was refluxed for 8 h, then concentrated in vacuo. The residue was dissolved in water (300 ml) and extracted with ethyl acetate (2×200 ml). The combined organic layers were washed with water (1×100 ml) and brine (1×100 ml), dried over MgSO$_4$, decolorized, filtered and concentrated in vacuo. The obtained crystalline product was recrystallized from diisopropyl ether (300 ml) to yield 70.12 g (82%) of the title compound.

Example 3

4-(5-p-methylphenyl-3-trifluoromethyl-pyrazol-1-yl)-benzenesulfonyl chloride

To a stirred suspension of 4-(5-p-methylphenyl-3-trifluoromethyl-pyrazol-1-yl)-benzenesulfonic acid (43 g, 0.112 mol) in dichloromethane (250 ml) phosphorous pentachloride (34.20 g, 0.168 mol) was added portion-wise at room temperature, followed by addition of N,N-dimethylformamide (10 ml). The so obtained suspension was refluxed for 8 h, then concentrated in vacuo. The residue was partitioned between ethyl acetate (150 ml) and water (150 ml) and separated. The aqueous phase was extracted with ethyl acetate (1×50 ml), the combined organic layers were dried over MgSO$_4$, filtered and concentrated. The obtained oil was crystallized from cyclohexane (120 ml) to yield 33.40 g (74%) of the title compound as white crystals. Mp: 97-98° C.

Example 4

N-hydroxy-4-(5-p-methylphenyl-3-trifluoromethyl-pyrazol-1-yl)-benzenesulfonamide

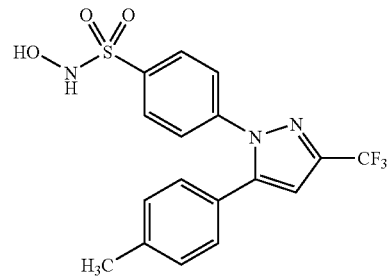

To a stirred suspension of hydroxylamine hydrochloride (2.74 g, 40 mmol) in dioxane (25 ml) sodium acetate (3.25 g, 40 mmol) in water (15 ml) was added dropwise at room temperature, followed by dropwise addition of 4-(5-p-methylphenyl-3-trifluoromethyl-pyrazol-1-yl)-benzenesulfonyl chloride (4.11 g, 10 mmol) in dioxane (40 ml). The obtained reaction mixture was poured into water (100 ml), extracted with ethyl acetate (2×50 ml), the organic layers were washed with water (3×50 ml) and brine (1×50 ml), dried over MgSO$_4$, filtered and concentrated in vacuo. The obtained oil was crystallized from 75% aqueous ethanol (75 ml) to yield 2.94 g (75%) of the title compound as white crystals. Mp: 203° C.

Example 5

(R,S)-2-[4-(5-p-methylphenyl-3-trifluoromethyl-pyrazol-1-yl)-benzensulfonylamino-oxy]-propionic acid

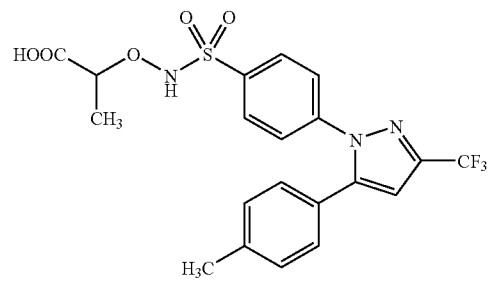

To a stirred suspension of 2-aminooxy-propionic acid hydrochloride (32.60 g, 0.23 mol) in dioxane (100 ml) sodium acetate (18.86 g, 0.23 mmol) in water (100 ml) was added dropwise at room temperature, followed by dropwise addition of 4-(5-p-methylphenyl-3-trifluoromethyl-pyrazol-1-yl)-benzenesulfonyl chloride (38 g, 94.80 mmol) in dioxane (100 ml). The obtained reaction mixture was stirred for 5 h, then concentrated in vacuo. The residue was dissolved in water (200 ml), extracted with ethyl acetate (2×100 ml), the combined organic layers were washed with water (4×50 ml) and brine (1×50 ml), dried over MgSO$_4$, filtered and concentrated in vacuo. The obtained oil was crystallized from toluene (250 ml) to yield 37.94 g (85%) of the title compound as white crystals. The so obtained product was dissolved in toluene (480 ml) and stirred at 0-5° C. for 1 h, the precipitated product was filtered off, washed with cold toluene and dried at room temperature to yield 36.43 g (96%) of the title compound. Mp: 187-189° C., HPLC: 99.9%.

Example 6

Disodium (R,S)-2-[4-(5-p-methylphenyl-3-trifluoromethyl-pyrazol-1-yl)-benzenesulfonyl-aminooxy]-propionic acid monohydrate

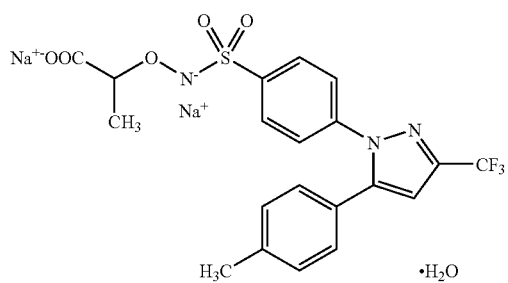

To a stirred solution of (+/−)-2-[4-(5-p-methylphenyl-3-trifluoromethyl-pyrazol-1-yl)-benzenesulfonylaminooxy]-propionic acid (35 g, 74.50 mmol) in ethanol (400 ml) 3.9 N sodium hydroxide solution (38.46 ml, 0.15 mol) was added at room temperature. The product started to precipitate after 5 minutes. The suspension was cooled to 0-5° C. and stirred for 2 h, the product was filtered off, washed with ethanol (50 ml) and dried at 60° C. to yield 38.39 g (96.7%) of the title compound.

Compounds of Examples of 7-16 were synthesized according to the methods described in Examples 5 and 6.

Example 7

[4-(5-p-methylphenyl-3-trifluoromethyl-pyrazol-1-yl)-benzenesulfonylaminooxy]-acetic acid

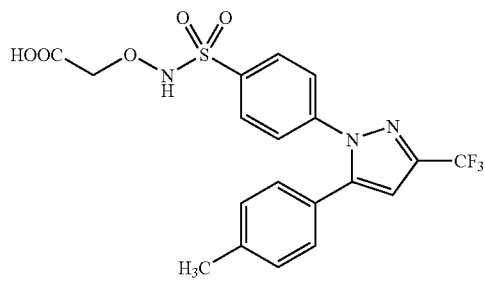

Yield: 88%. Mp: 224-225° C.

Example 8

[4-(5-p-methylphenyl-3-trifluoromethyl-pyrazol-1-yl)-benzenesulfonylaminooxy]-acetic acid ethyl ester

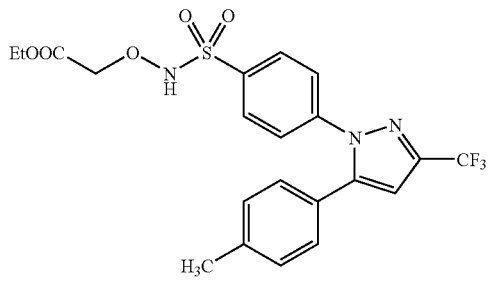

Yield: 82%. Mp: 143-144° C.

Example 9

3-[4-(5-p-methylphenyl-3-trifluoromethyl-pyrazol-1-yl)-benzenesulfonylaminooxy]-propionic acid

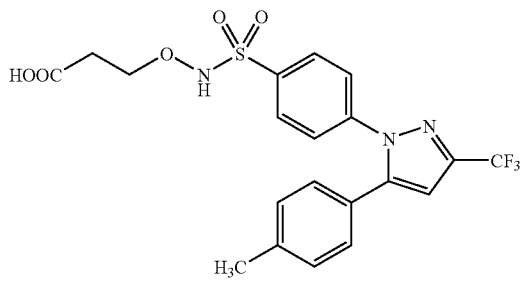

Yield: 92%. Mp: 176-178° C.

Example 10

2-[4-(5-p-methylphenyl-3-trifluoromethyl-pyrazol-1-yl)-benzenesulfonylaminooxy]-propionic acid ethyl ester

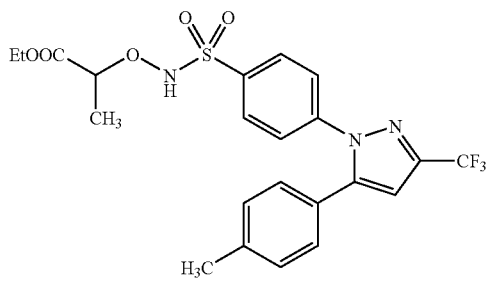

Yield: 82%. Mp: 137-138° C.

Example 11

N-acetoxy-4-(5-p-methylphenyl-3-trifluoromethyl-pyrazol-1-yl)-benzenesulamide

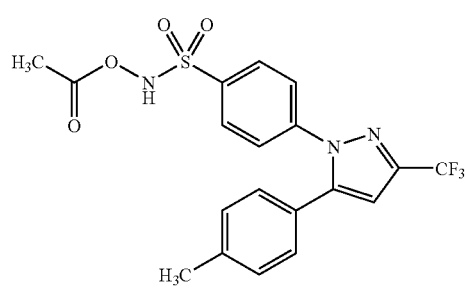

Yield: 44%. Mp: 138-140° C.

Example 12

N-benzoyloxy-4-(5-p-methylphenyl-3-trifluoromethyl-pyrazol-1-yl)-benzenesulfonamide

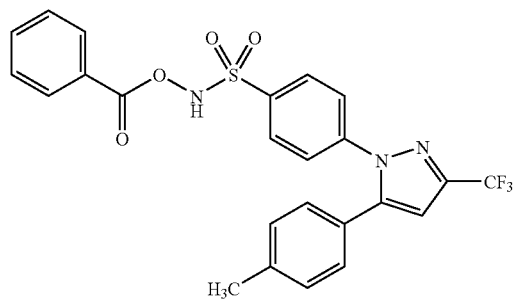

Yield: 40%. Mp: 152-155° C.

Example 13

N-pivaloyloxy-4-(5-p-methylphenyl-3-trifluoromethyl-pyrazol-1-yl)-benzenesulfonamide

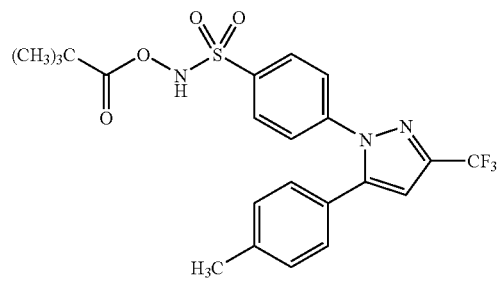

Yield: 72%. Mp: 134-136° C.

Example 14

Sodium [4-(5-p-methylphenyl-3-trifluoromethyl-pyrazol-1-yl)-benzenesulfonyl-aminooxy]-acetic acid trihydrate

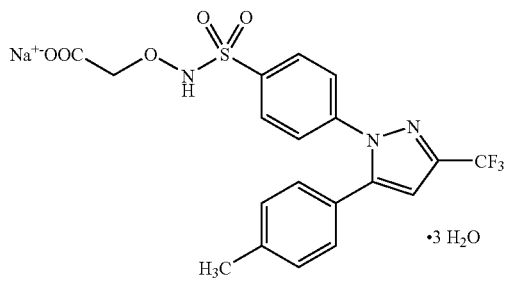

Yield: 90%.

Example 15

Disodium 3-[4-(5-p-methylphenyl-3-trifluoromethyl-pyrazol-1-yl)-benzenesulfonyl-aminooxy]-propionic acid monohydrate

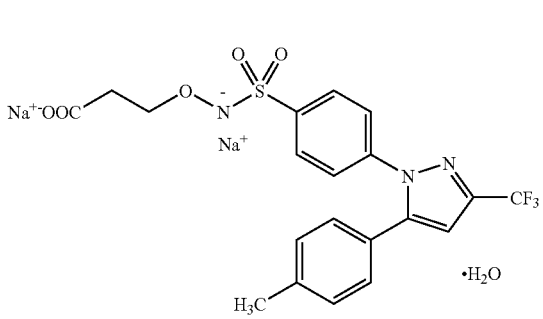

Yield: 87%.

Example 16

Disodium 2-methyl-2-[4-(5-p-methylphenyl-3-trifluoromethyl-pyrazol-1-yl)-benzenesulfonylaminooxy]-propionic acid monohydrate

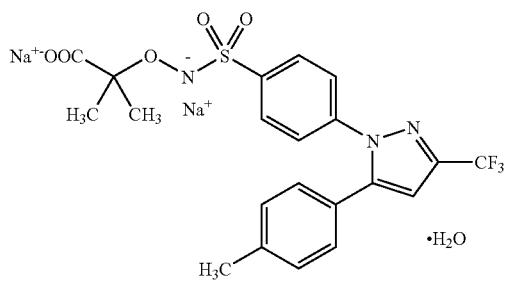

Yield: 53%.

Example 17

(−)-2-[4-(5-p-methylphenyl-3-trifluoromethyl-pyrazol-1-yl)-benzenesulfonyl-aminooxy]-propionic acid To a stirred solution of (+/−)-2-[4-(5-p-methylphenyl-3-trifluoromethyl-pyrazol-1-yl)-benzenesulfonyl-aminooxy]-propionic acid (10 g, 21 mmol) in 97% ethanol (50 ml) (−)-ephedrine (1.76 g, 10 mmol) was added. The mixture was stirred at room temperature for 1 day, the precipitated crystals were filtered off and washed with 97% ethanol to yield 3.38 g (25%) product, calculated on the basis of the starting racemic mixture. The so obtained crystals were recrystallized twice from 97% ethanol to yield 2.02 g (60%) white crystalline material.

The diastereomer salt was suspended in ethyl acetate (30 ml) and 1 N hydrochloric acid (15 ml) was added. The organic layer was separated, dried over MgSO₄, filtered and concentrated in vacuo. The obtained oil was crystallized from petroleum ether to yield 0.9 g (60%) of the title compound.

Mp: 158-160° C. $[\alpha]_D = -505.3°$ (c=1, methanol)

Example 18

(+)-2-[4-(5-p-methylphenyl-3-trifluoromethyl-pyrazol-1-yl)-benzenesulfonyl-aminooxy]-propionic acid The title compound was obtained according to the method described in Example 17 using (+)-ephedrine as resolving agent and isopropanol as solvent.

Yield: 0.62 g. Mp: 161-163° C. $[\alpha]_D = +457.6°$ (c=1, methanol)

What we claim is:

1. A compound of formula (I),

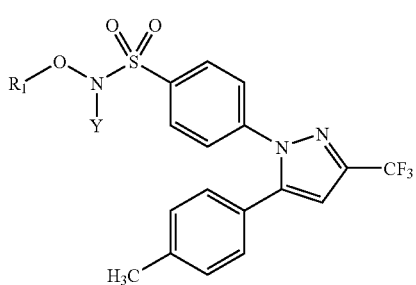

(I)

wherein $R_1$ is a hydrogen atom, $C_1$-$C_5$ acyl group, benzoyl group or $R_2$—COOR₃ group, Y is hydrogen atom or an alkali metal ion, $R_2$ is a $C_1$-$C_4$ straight or branched alkylidene group and $R_3$ is a hydrogen atom, $C_1$-$C_4$ alkyl group or alkali metal ion, including a stereoisomer or diasteromer thereof, or a pharmaceutically acceptable salt, or solvate thereof.

2. (R,S)-2-[4-(5-p-methylphenyl-3-trifluoro-methyl-pyrazol-1-yl)-benzenesulfonyl-aminooxy]-propionic acid, as defined in claim 1, including a stereoisomer or diasteromer thereof, or a pharmaceutically acceptable salt, or solvate thereof.

3. Disodium (R,S)-2-[4-(5-p-methylphenyl-3-trifluoromethyl-pyrazol-1-yl)-benzenesulfonyl-aminooxy]-propionic acid monohydrate as defined in claim 1.

4. A process for preparing a compound of the Formula (I)

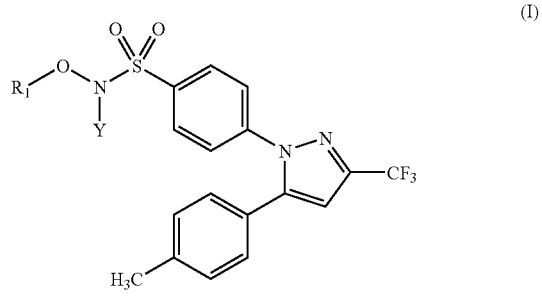

(I)

wherein $R_1$ is a hydrogen atom, $C_1$-$C_5$ acyl group, benzoyl group or $R_2$—COOR₃ group, Y is a hydrogen atom or an alkali metal ion, $R_2$ is a $C_1$-$C_4$ straight or branched alkylidene group and $R_3$ is a hydrogen atom, $C_1$-$C_4$ alkyl group or alkali metal ion, including a stereoisomer or diasteromer thereof, or a pharmaceutically acceptable salt, or solvate thereof which comprises the steps of:

(a) reacting 4,4,4-trifluoro-1-(4-methyl-phenyl)-butane-1,3-dione with p-hydrazino-benzenesulfonic acid in an inert solvent in the presence of hydrochloric acid to obtain a compound of the Formula (III)

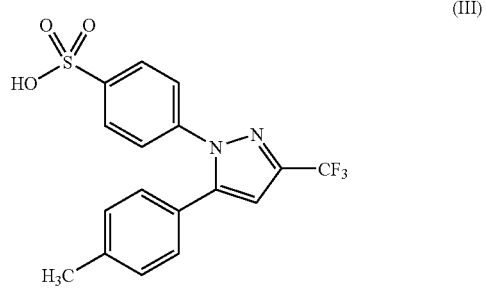

(III)

(b) reacting the obtained compound of formula (III) with phosphorus pentachloride in an inert solvent to give a compound of formula (II)

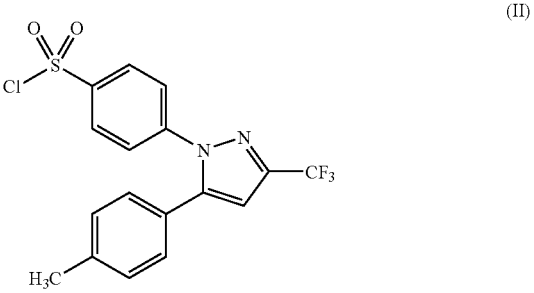

(II)

and, (c) reacting the obtained compound of the Formula (II)
(i) with hydroxylamine to obtain a compound of the Formula (I) where $R_1$ is hydrogen, or
(ii) with a compound of formula NH₂—O—$R_2$—COOR₃, wherein the meanings of $R_2$ and $R_3$ are as defined herein above, to obtain a compound of the Formula (I) where $R_1$ is $R_2$—COOR₃, or (iii) with a compound of formula $NH_2$—$OCOR_1$, wherein the meaning of $R_1$ is the same as mentioned before to yield a compound of the Formula (I) where $R_1$ is a $C_1$-$C_5$ acyl group or a benzoyl group.

5. An anti-inflammatory and analgesic pharmaceutical composition which comprises a therapeutically effective amount for treating inflammation and pain of the compound of the Formula (I) as defined in claim 1, including a stereoisomer or diasteromer thereof, or a pharmaceutically acceptable salt, or solvate thereof as well as at least one pharmaceutically acceptable inert adjuvant or auxiliary material.

6. A method of treatment of inflammation and pain in a mammalian subject in need of said treatment, which comprises the step of administering to said mammalian subject a therapeutically effective amount of the compound of the Formula (I) as defined in claim 1 including a stereoisomer or diasteromer thereof, or a pharmaceutically acceptable salt, or solvate thereof.

7. The method of treating inflammation and pain defined in claim 6 wherein the compound of the Formula (I) including a stereoisomer or diasteromer thereof, or a pharmaceutically acceptable salt, or solvate thereof is administered to the mammalian subject by oral, parenteral, buccal, sublingual, nasal, rectal, or transdermal administration.

8. 4-(5-p-methyl-phenyl)-3-trifluoromethyl-pyrazol-1-yl)-benzenesulfonic acid.

* * * * *